United States Patent
Ito et al.

(10) Patent No.: US 7,282,479 B2
(45) Date of Patent: Oct. 16, 2007

(54) HYPERTHERMIA AGENT FOR MALIGNANT TUMOR COMPRISING CYTOKINE AND MAGNETIC FINE PARTICLES

(75) Inventors: Akira Ito, Nagoya (JP); Hiroyuki Honda, Nagoya (JP); Takeshi Kobayashi, 29-1, Shimokata-cho 4-chome, Chikusa-ku, Nagoya-shi, Aichi (JP)

(73) Assignees: TTC Co., Ltd., Tokyo (JP); Takeshi Kobayashi, Aichi (JP)

( * ) Notice: Subject to any disclaimer, the term of this patent is extended or adjusted under 35 U.S.C. 154(b) by 105 days.

(21) Appl. No.: 10/815,273

(22) Filed: Mar. 31, 2004

(65) Prior Publication Data

US 2004/0219130 A1 Nov. 4, 2004

Related U.S. Application Data

(60) Provisional application No. 60/459,069, filed on Mar. 31, 2003.

(51) Int. Cl.
*A61K 38/19* (2006.01)

(52) U.S. Cl. .......................................... 514/6; 424/646

(58) Field of Classification Search ..................... None
See application file for complete search history.

(56) References Cited

OTHER PUBLICATIONS

Yanase et al (Jpn J Cancer Research, 1998, 89:463-470).*
O'Day et al (Clinical Cancer Research, 2002, 8:2775-2781).*
Ito et al (Cancer Gene Therapy, 2001, 8:649-654).*
Shinkai et al I (Biotechnol Appl Biochem, 1994, 21:125-137, IDS).*
Shinkai et al II (Jpn J Hyperthermic Oncol, 1994, 10:177, IDS, abstract only).*
Ito et al (J of Bioscience and Bioengineering, 2005, 100:1-11).*
Shinkai, et al., "Antibody-conjugated magnetoliposomes for targeting cancer cells and their application in hyperthermia", Biotechnol. Appl. Biochem. 21, pp. 125-137, 1994.
Shinkai, et al., "Heat properties of magnetoliposomes for local hyperthermia", Jpn. J. Hyperthermic Oncol. 10(2), pp. 168-177, 1994. (Abstract translation only).

* cited by examiner

*Primary Examiner*—Shanon Foley
*Assistant Examiner*—Laura B Goddard
(74) *Attorney, Agent, or Firm*—Jordan and Hamburg LLP

(57) ABSTRACT

The present invention discloses a hyperthermia agent for malignant tumor which comprises cytokine or a vector in which a cytokine gene is integrated so that cytokine can express in malignant tumor cells, and magnetic fine particles, and a hyperthermia method using the same.

12 Claims, 12 Drawing Sheets

(2 of 12 Drawing Sheet(s) Filed in Color)

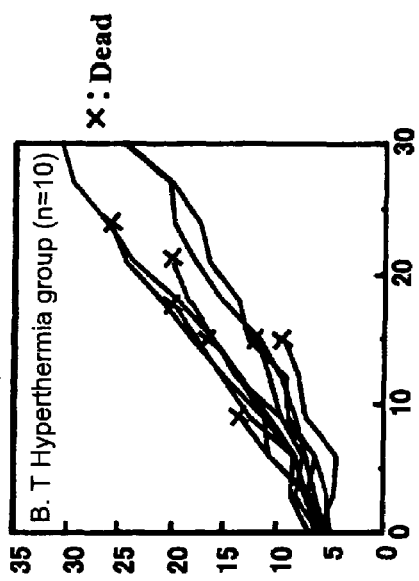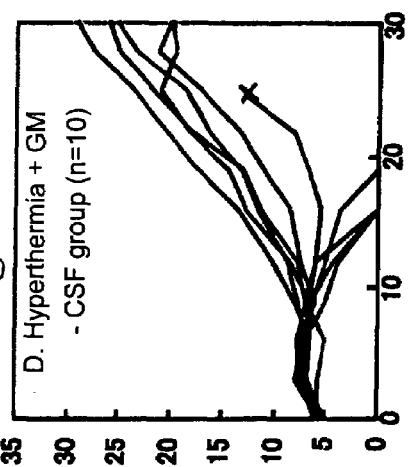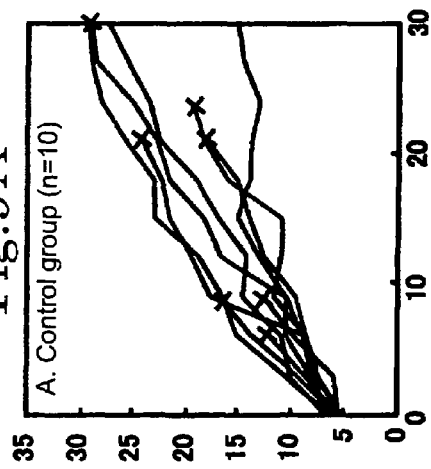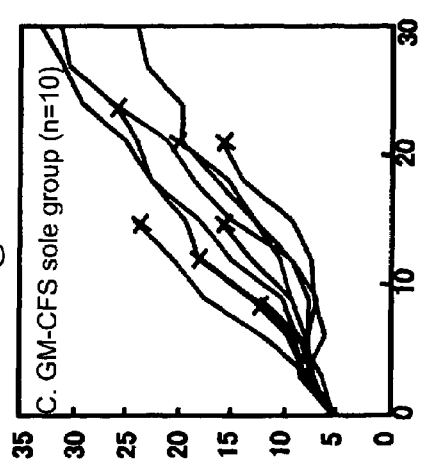
Fig.9A A. Control group (n=10)
Fig.9B B. T Hyperthermia group (n=10) ×: Dead
Fig.9C C. GM-CFS sole group (n=10)
Fig.9D D. Hyperthermia + GM-CSF group (n=10)
Size of tumor (mm) vs. Days after MCL injection (day)

a. At the time of injection of MCL b. At the time of completely regressed
(Group D : 30days after injection of MCL)

c. At the time of tumor increased
(Group A : 30days after injection of MCL)

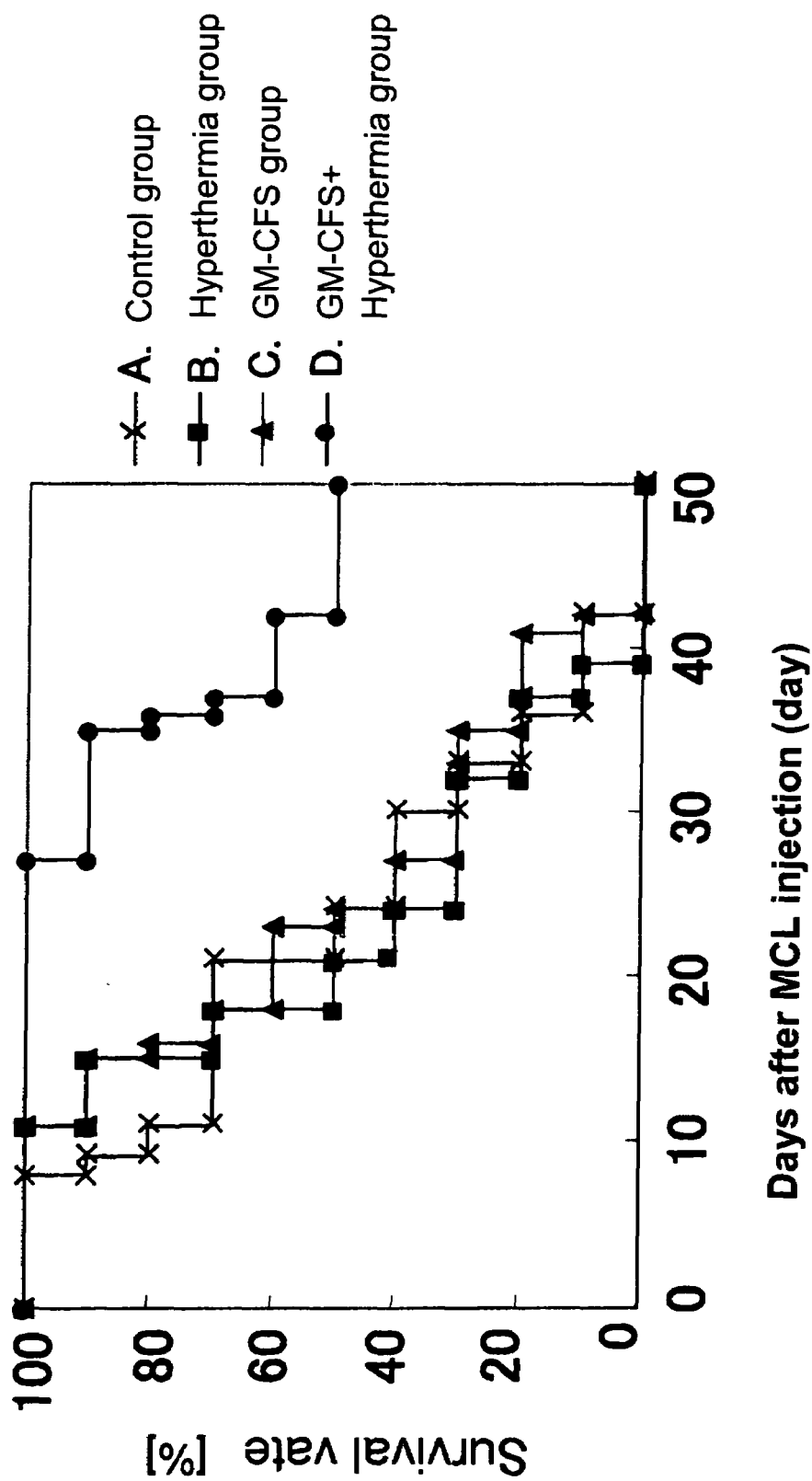

Fig. 12A
Fig. 12B
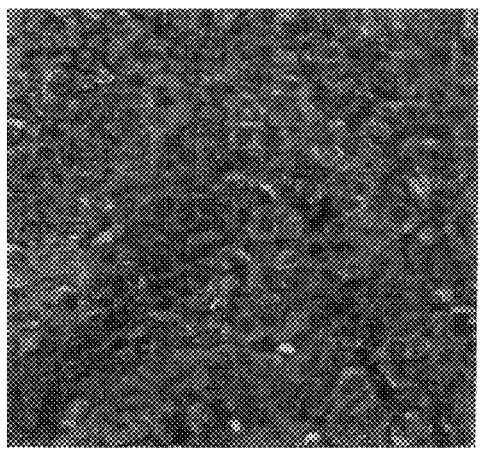
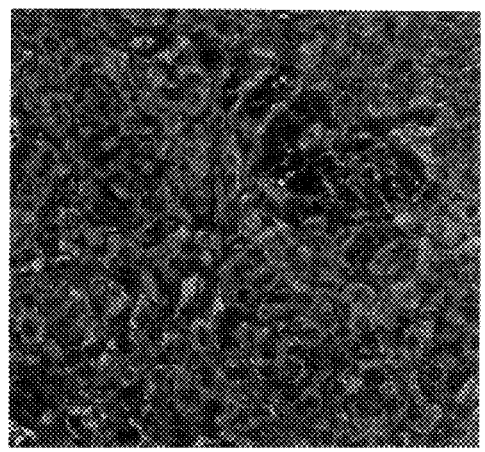
a. Tumor tissue of control group
(Group A)
b. Tumor tissue of thermatology
group (Group B)

HYPERTHERMIA AGENT FOR MALIGNANT TUMOR COMPRISING CYTOKINE AND MAGNETIC FINE PARTICLES

REFERENCE TO RELATED APPLICATION

Priority is hereby claimed under 35 U.S.C. 119(e) based on Provisional Application Ser. No. 60/459,069, filed Mar. 31, 2003.

TECHNICAL FIELD

The present invention relates to a hyperthermia agent for malignant tumor, more specifically to a hyperthermia agent for malignant tumor containing cytokine and magnetic fine particles.

BACKGROUND ART

For the treatment of malignant tumor, surgical therapy, radiotherapy, and chemotherapy by an anticancer agent have been mainly used as of today. Diagnostic technology and clinical technology have markedly progressed, so that it is not impossible to treat malignant tumors.

However, at present, a ratio of malignant tumors occupied in a cause of death exceeds 30%, and development of a novel therapeutic method against malignant tumors has been desired. Thus, as a novel therapeutic method, development of gene therapy, immunotherapy, hyperthermia, etc. has been started.

Among the above-mentioned novel therapeutic methods for malignant tumors, hyperthermia is an old therapeutic method which has been carried out from ancient Greece and is a therapeutic method which utilizes a property that malignant tumor cells are weaker to heat than normal cells. That which has widely been used as the hyperthermia is a method in which a portion existing a tissue of malignant tumor is entirely heated to kill the malignant tumor cells which are weak against heat.

As a hyperthermia for malignant tumor, it has been known a method in which magnetic fine particles are used as an internal heating element, and the magnetic fine particles are heated by electromagnetic wave. In order to increase therapeutic effect by uniformly heating the malignant tumor tissue, it has been known to use magnetic magnetite as magnetic fine particles, and to prepare a magnetite cationic liposome (MCL) by coating the magnetite with a lipid membrane (liposome) having a positive charge to increase an intake efficiency of the magnetite into the malignant tumor cells since the surfaces of the malignant tumor cells are charged to negative and to use the same (Shinkai et al., Jpn. J. Hyperthermic Oncol., vol. 10, pp. 168-177 (1994) and Shinkai et al., Biotech. Appl. Biochem., vol. 21, pp. 125-137 (1994)).

A hyperthermia for malignant tumor has been attracted attention since it is a noninvasive therapeutic method, but this hyperthermia is difficult to completely treat various kinds of malignant tumors in many cases when it is used alone.

Accordingly, an improved hyperthermia which can treat various kinds of malignant tumors more effectively has been required.

DISCLOSURE OF THE INVENTION

The present invention has accomplished by finding out that, in hyperthermia of malignant tumor, in particular, in hyperthermia of malignant tumor using magnetic fine particles, cytokine is stimulated by immunologically competent cells and activated, whereby the therapeutic effects are markedly improved.

That is, the present invention relates to a hyperthermia agent for malignant tumor which comprises cytokine and magnetic fine particles.

Also, it has been found that the same effects as mentioned above can be obtained even when a cytokine in which a cytokine gene is expressed in malignant tumor cells is used.

Accordingly, the present invention further relates to a hyperthermia agent for malignant tumor which comprises a vector in which a cytokine gene is integrated so that cytokine can express in malignant tumor cells, and magnetic fine particles.

The hyperthermia agent of the present invention may contain the cytokine and the magnetic fine particles, or the vector into which the cytokine gene is integrated and the magnetic fine particles, simultaneously, or separately.

BRIEF DESCRIPTION OF THE DRAWINGS

Color Drawings

The patent or application file contains at least one drawing executed in color. Copies of this patent or patent application publication with color drawing(s) will be provided by the U.S. Patent and Trademark Office upon request and payment of the necessary fee.

FIG. 5A is a control group, FIG. 5B is a hyperthermia group, FIG. 5C is a IL-2 alone group, and FIG. 5D is a thermotology+IL-2 group.

FIG. 9 is a drawing showing a size of tumor with a lapse of time after initiation of therapy in Example 2, FIG. 9A is a control group, FIG. 9B is a hyperthermia group, FIG. 9C is a GM-CSF alone group, and FIG. 9D is a hyperthermia+GM-CSF group.

FIG. 10 is a drawing showing therapeutic effects by combination therapy in Example 2.

FIG. 11 shows a survival rate of cancer-carried mouse during 90 days after hyperthermia in Example 2. A (control) group (n=10): X; B (hyperthermia) group (n=10): ■; C (GM-CSF) group (n=10): ▲; D (hyperthermia+GM-CSF) group (n=10): ●.

FIG. 12 is a drawing showing a stained state by Hsp70 of a tumor tissue in Example 2, FIG. 12A is a drawing showing a tumor tissue of a control group, FIG. 12B is a drawing showing a tumor tissue of a hyperthermia group.

BEST MODE FOR CARRYING OUT THE INVENTION

Figure 2:
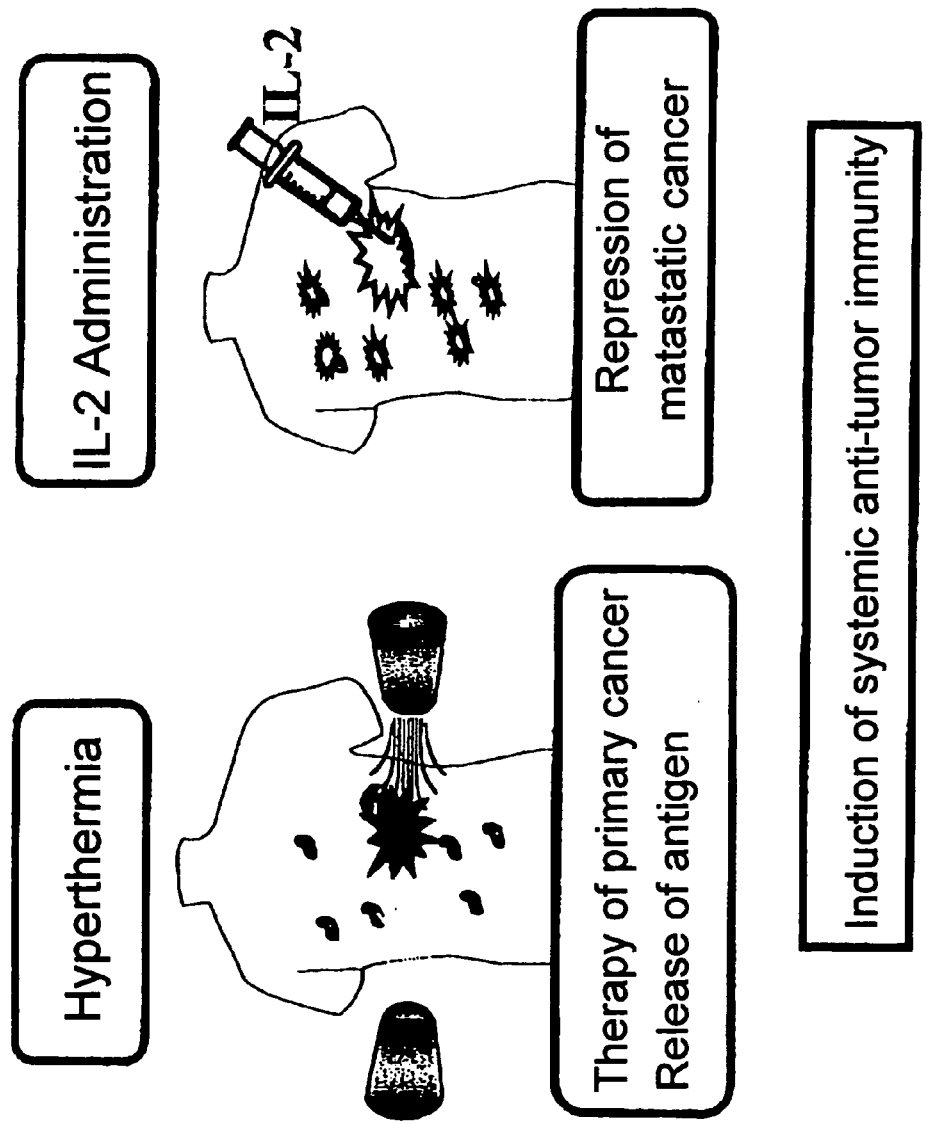
FIG. 2 is a schematic drawing of therapy of melanoma by administration of IL-2 of the present invention.

The cytokine to be used in the present invention is prepared mainly from immunologically competent cells, and is a polyfunctional cell growth and differentiation-inducing factor that controls an immunological reaction and a hematopoietic reaction. These series of factor groups are mainly produced by activated T cells, macrophages or stroma cells, and connect lymphocytes and hematopoietic type cells like a network, so that their growth, differentiation and function are controlled. Such a cytokine is not specifically limited so long as it can accomplish the effects of the present invention, and it may be exemplified by, for example, interleukin-2 (IL-2), GM-CSF (granulocyte macrophage colony stimulating factor) that is a cytokine having a stimulating effect for growth and differentiation of granule type precursor cells, interleukin-4 (IL-4), interleukin-12 (IL-12), interferon-β (IFN-β), interferon-γ (IFN-γ), tumor necrosis factor (TNF)-α, etc., particularly preferably IL-2, GM-CSF and IL-12. IL-2 is produced by activated helper T cells, and strengthen growth and activation of immunologically competent cells such as NK (Natural Killer) cells, cytotoxic T cells and macrophage. As a therapeutic method using IL-2, there may be mentioned a sole administration or a method in which lymphocytes are co-cultivated with IL-2 in vitro to induce LAK (lymphokine activated killer) cells and returned in a body. A schematic drawing of therapy of melanoma by administration of IL-2 is shown in FIG. 2.

Also, a method of producing the cytokine to be used in the present invention is not specifically limited, and the cytokine includes that derived from natural, that obtained by genetic recombination, that obtained by chemical synthesis, etc.

As the magnetic fine particles to be used in the present invention, any materials may be used so long as it absorbs electromagnetic wave to cause heat generating reaction and harmless to human body. It is particularly advantageous to use one that causes heat generating reaction by absorbing electromagnetic wave with frequencies that are difficultly absorbed by human body. Of these, ferromagnetic fine particles are preferably used since absorption efficiency of the electromagnetic wave is good, and for example, it may be exemplified by ceramics such as magnetite, ferrite, etc., or ferromagnetic metal such as permalloy, etc.

Incidentally, the above-mentioned magnetic fine particles are desirably having a particle size of 5 μm or less, particularly 1 μm or less.

Figure 1:
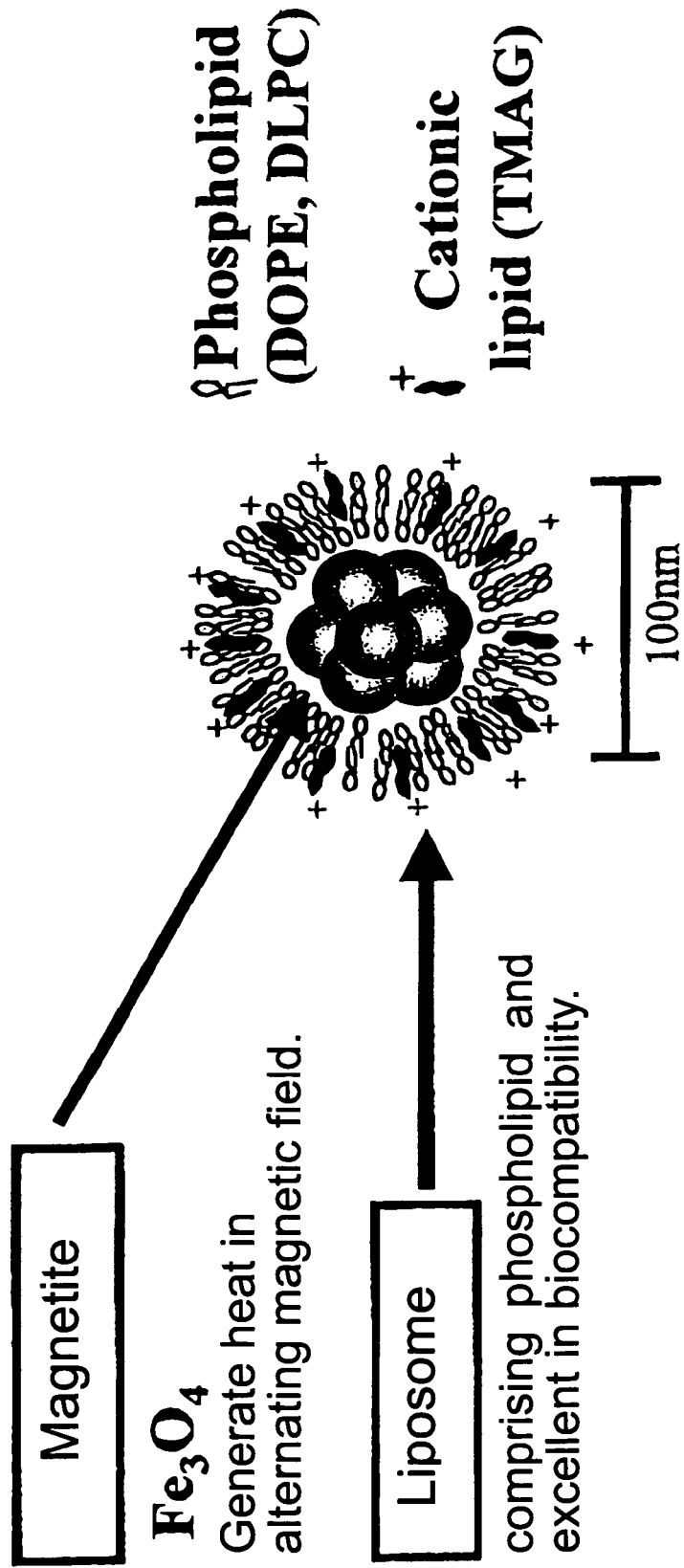
FIG. 1 is a drawing showing a structure of magnetite cationic liposome (MCL).

As the preferred magnetic fine particles to be used in the present invention, magnetite cationic liposome (MCL) prepared by utilizing a lipid film (liposome) having a positive charge and coating magnetic magnetite therewith is preferably used. A structure of the MCL is shown in FIG. 1. Since the surfaces of the malignant tumor cells are charged negative, the MCL is selectively concentrated to the malignant tumor cells. When the MCL is directly injected to the malignant tumor, it can be confirmed that it is taken into the malignant tumor cells by endocytosis.

Also, as the magnetic fine particles preferably used in the present invention, there may be mentioned magnetic fine particles on the surface of which is bound an antibody that selectively binds to the malignant tumor cells. The magnetic fine particles to which an antibody is bound are selectively concentrated at the neighbor of the malignant tumor cells, so that hyperthermia can be carried out without heating cells other than the malignant tumor cells.

A vector into which a cytokine gene is integrated so that it can express cytokine to be used as a therapeutic agent of the present invention in the malignant tumor cells can be obtained by integrating the cytokine gene into a vector such as a plasmid and a virus, etc., with a suitable regulator gene, so that it is capable of expressing.

The present invention also relates to a use of cytokine in hyperthermia of malignant tumor. That is, the present invention relates to a hyperthermia method of malignant tumor which comprises administering cytokine to malignant tumor, and then subjecting the malignant tumor to hyperthermia, in particular, it relates to a hyperthermia method of malignant tumor which comprises administering cytokine and magnetic fine particles to malignant tumor, and then, placing the malignant tumor in a magnetic field. The cytokine and the magnetic fine particles can be administered to the malignant tumor simultaneously, or separately with a suitable interval, and desirably they are simultaneously administered. The cytokine and the magnetic fine particles are desirably administered at the malignant tumor tissue and neighbor thereof.

The present invention further relates to a use of a cytokine gene in hyperthermia of malignant tumor. That is, it relates to a hyperthermia method of malignant tumor which comprises injecting a vector into which a cytokine gene is integrated, so that it can express the cytokine in malignant tumor cells, into malignant tumor whereby expressing the cytokine in the malignant tumor cells, then subjecting the malignant tumor tissue to hyperthermia. In particular, the present invention relates to a hyperthermia method of malignant tumor which comprises injecting a vector into which a cytokine gene is integrated, so that it can express the cytokine in malignant tumor cells, into malignant tumor whereby expressing the cytokine in the malignant tumor cells, and then, after administering the magnetic fine particles to the malignant tumor, placing the malignant tumor in a magnetic field. Administration of the magnetic fine particles to malignant tumor is preferably carried out after the cytokine is sufficiently expressed in the malignant tumor cells.

In the malignant tumor according to the present invention, all kinds of malignant tumors are contained, and there may be mentioned, for example, skin cancer such as malignant melanoma, lung cancer, large intestine cancer, breast cancer, brain tumor, malignant tissue glomus tumor, osteosarcoma, liver cancer, prostate cancer, pancreas cancer, esophagus cancer, bladder cancer, ovarian cancer, uterine cancer, stomach cancer, etc., it is preferably applied to malignant melanoma, lung cancer, prostate cancer, large intestine cancer, particularly preferably applied to malignant melanoma.

As the magnetic field to be used in the therapeutic method of the present invention, a high frequency magnetic field is preferably used, and a high frequency magnetic field with an electromagnetic wave having a frequency of 1 KHz to 10 MHz is particularly preferred. The reason why the high frequency magnetic field with a frequency higher than 1 KHz is preferred is that a heating efficiency due to magnetic hysteresis is high, and the reason why the high frequency magnetic field with a frequency lower than 10 MHz is preferred is that the magnetic fine particles can be heated while a heat generating reaction of a living thing due to induction current can be controlled.

The magnetic fine particles to which an antibody which selectively binds to the malignant tumor cells is bound on the surface thereof to be used in the present invention can be produced by, for example, the method disclosed in Japanese Provisional Patent Publication No. Hei. 3-128331, that is, by binding a bifunctional cross-linking agent to the magnetic fine particles, and then, an antibody which selectively binds to the malignant tumor cells is reacted therewith.

As the antibody which selectively binds to the above-mentioned malignant tumor cells, there may be used, for example, a monoclonal antibody (HB4C5) against lung cancer, a monoclonal antibody (17-1A) against large intestine cancer, a monoclonal antibody (H15F2) against breast cancer, a monoclonal antibody (CH149) against malignant melanoma, and the like.

When the above-mentioned magnetic fine particles are ferromagnetic metal, it is advantageous to bind the bifunctional cross-linking agent after forming an oxidation film on the surface thereof by applying an oxidation treatment to the above-mentioned ferromagnetic metal.

As a method for binding the above-mentioned bifunctional cross-linking agent, for example, it is advantageous to use a method of biding γ-aminopropyltriethoxysilane and glutaraldehyde to the magnetic fine particles in this order, a method of binding vinyl aldehyde and acryl aldehyde in this order, or a method of binding aminosilane and polyethylene glycol in this order, etc.

EXAMPLES

In the following, the present invention is explained by referring to Examples, but the present invention is not limited by these.

Example 1

Administration of IL-2

1 Experimental Materials and Experimental Method 1-1 Malignant Tumor Cell and Experimental Animals As model cancer cells, mouse B16 melanoma cells were used. Passage was carried out by using 100 mm of tissue culture dish (available from IWAKI) in which 10 ml of a medium had been placed, in an incubator to which 5% carbon dioxide had been added at 37° C. As the medium, Dulbecco's Modified Eagle Medium (DMEM) containing 10% fetal bovine serum, $NaHCO_3$, HEPES, 5 mM of non essential amino acid and antibiotics (penicillin G potassium and streptomycin sulfate) was used.

1-2 Transplantation of Cancer Cell B16

B16 melanoma cells cultured on a dish were peeled off from the dish by a treatment with trypsin. $6 \times 10^6$ cells were suspended in 10 ml of tissue culture medium having the above-mentioned composition, and recovered by ultracentrifugation and washed with a phosphate buffered saline (PBS). Then, these cells ($2 \times 10^6$) were dispersed with about 200 μl of PBS, and then, the cells suspended liquor was transplanted subcutaneously to a right leg of C57BL/6 mouse (female, 4-weeks old) which is a model animal by using a scalp vein needle (25G×⅝″) (available from Terumo Corporation). Nembutal (available from Dainippon Pharmaceutical Co., Ltd.) was used for anesthesia and administered to abdominal cavity.

1-3 Preparation Method of Magnetite Cationic Liposome (MCL)

The following were used as reagents.

Magnetic fine particles: 10 nm magnetite (available from Toda Kogyo Corporation)

TMAG: N-(α-trimethylammonioacetyl)-didodecyl-D-glutamate chloride (available from Sogo Pharmaceutical Co., Ltd.)

DLPC: Dilauroylphosphatidylcholine (available from SIGMA)

DOPE: Dioleylphosphatidylethanolamine (available from SIGMA)

The magnetite which is magnetic fine particles is used those having a particle size of 10 nm. The magnetite was thoroughly washed with deionized water to remove excessive ion components and subjected to ultrasonic wave treatment whereby a magnetite liquor which disperses in water was prepared. A phospholipid was prepared at an inside of an eggplant shaped flask with a composition of TMAG (5.56 mg), DLPC (11.17 mg) and DOPE (13.27 mg). To this phospholipid was added 2 ml of the magnetite liquor (20 mg-Fe/ml) prepared by the method as mentioned above, and the membrane was swelled by effecting vortex stirring. To the swelled membrane and the magnetic fine particles were applied an ultrasonic wave treatment for 15 minutes (28W), and then, 200 μl of 10-fold concentration physiological saline (PBS) was added thereto to make them in a state that they are dispersing in the physiological saline. Moreover, an ultrasonic wave treatment was further carried out for 15 minutes (28W) to obtain a magnetite cationic liposome (MCL).

Figure 3:
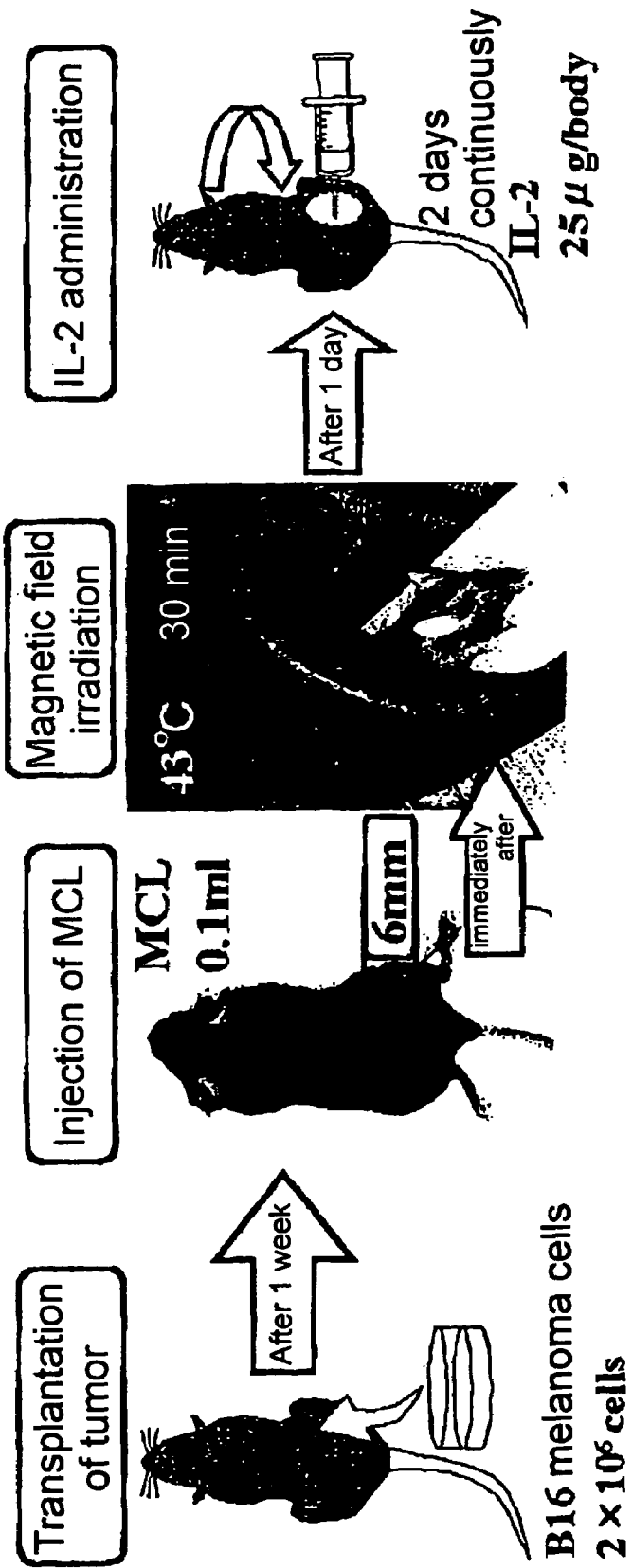
FIG. 3 is a drawing showing an outline of a therapeutic manner of the present invention in Example 1.

Summary of preparation of MCL is shown in FIG. 3.

1-4 Therapeutic Method

Administration of MCL

MCL (20 mg-Fe/ml) was injected into the tumor in an amount of 0.1 ml (Fe amount: 2 mg) at the time when a longer diameter of the tumor portion reached to 6 mm or so. Injection of MCL was carried out directly to the tumor portion by using a scalp vein needle (25G×⅝″) (available from Terumo Corporation). An injection speed was made 0.15 ml/30 min. Also, to prevent from leakage of MCL from syringe hole, it was allowed to stand after 30 minutes from injection.

Irradiation of High Frequency Magnetic Field

After transplantation of B16 melanoma cells, experimental animals were divided into four groups. In Group A, MCL alone was administered as a control group, and no irradiation of high frequency magnetic field was carried out. Group B was made a hyperthermia group, and immediately after administration of MCL, high frequency magnetic field was once irradiated to carry out hyperthermia. The magnetic field treatment was carried out by controlling an output of a magnetic field generating device, and heat generation of the magnetite was controlled at 43° C. for 30 minutes by changing a magnetic flux density. At this time, a horizontal type coil was used, and the tumor portion was placed at the center of the coil. Temperatures at the surface of the tumor and rectum during magnetic field irradiation were measured by using an optical fiber thermometer.

Administration of IL-2

As interleukin-2 (IL-2), IL-2, human, recombinant available from Wako Pure Chemical Industries, Ltd. was used. Preparation method of IL-2 is that IL-2 (50 μg) was dissolved in 50 μl of 100 mM acetic acid, diluted with PBS (containing 1% BSA), and finally made 300 μl of a solution (specific activity: 1×10⁵ units). Administration of IL-2 was carried out by administering it in an amount of 150 µl (5×10⁴ units) to the tumor portion of the mouse for 2 days continuously.

With regard to the remaining two groups, Group C was an IL-2 administered group, and after administration of MCL, IL-2 (150 µl) was directly administered to the tumor portion by using a scalp vein needle in the same manner as administration of MCL at the first and the second days. Group D was a group using the hyperthermia and IL-2 in combination, and immediately after administration of MCL, a high frequency magnetic field was once irradiated at 43° C. for 30 minutes, and at the next day, administration of IL-2 was carried out for 2 days continuously.

Summary of manner of therapy is shown in FIG. 3.

1-5 Results 1-5-1 Temperature Change During Magnetic Field Irradiation

Figure 4:
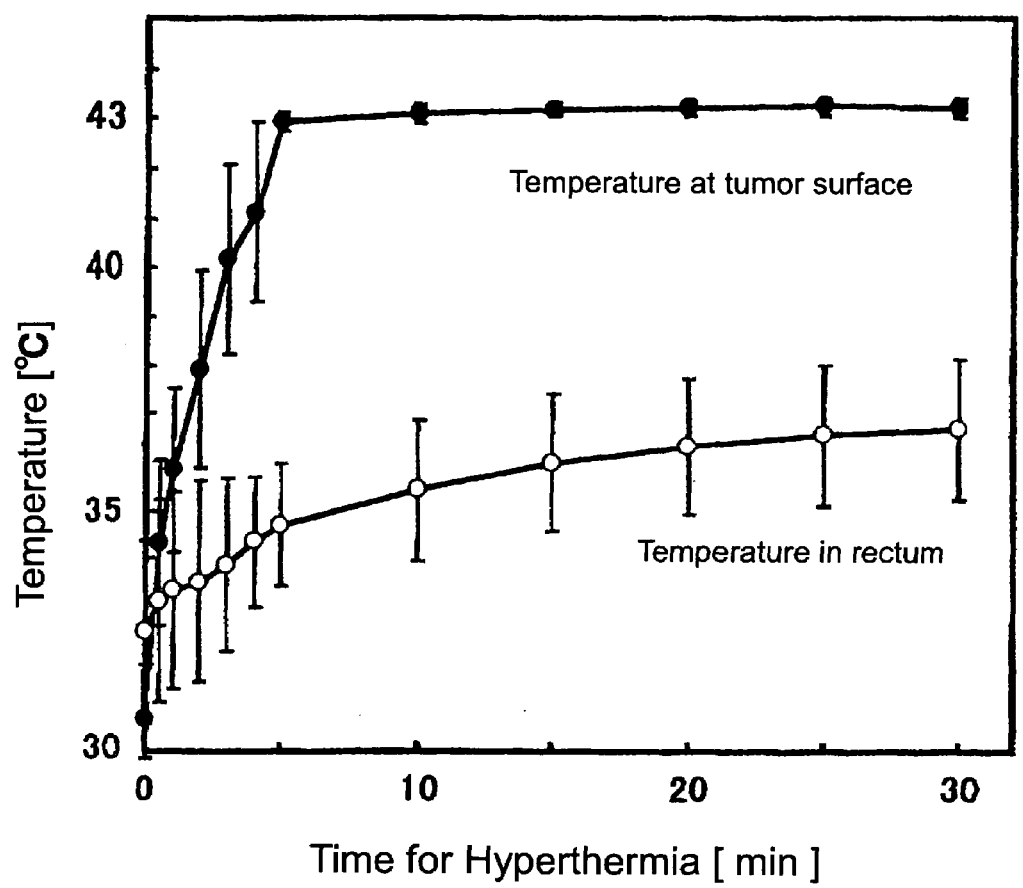
FIG. 4 is a drawing showing temperature change in magnetic field irradiation in Example 1.

Temperature change during magnetic field irradiation is shown in FIG. 4. A temperature of the tumor surface was raised to around 43° C. which is generally considered to be effective in the hyperthermia within a few minutes, and maintained at 43° C. constantly by controlling an output, whereby heating could be carried out for 30 minutes. To the contrary, a temperature in rectum was substantially the constant and not raised during irradiation of the magnetic field.

From the above fact, it can be understood that by applying hyperthermia using MCL to melanoma, the tumor tissue alone can be specifically heated and excessive temperature raising of the normal tissue can be prevented.

1-5-2 Change in a Size of Tumor with a Lapse of Time

Figure 5:
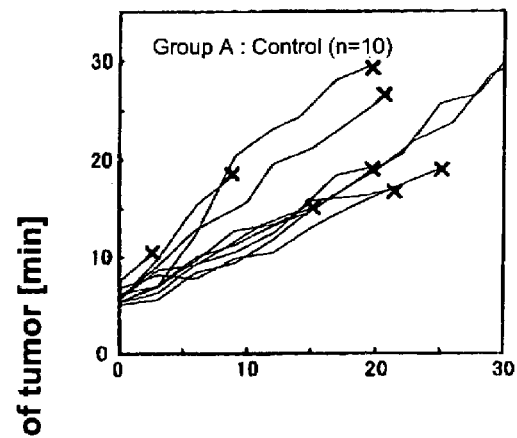
FIG. 5 is a drawing showing a size of tumor with a lapse of time after initiation of therapy in Example 1.
Figure 5:
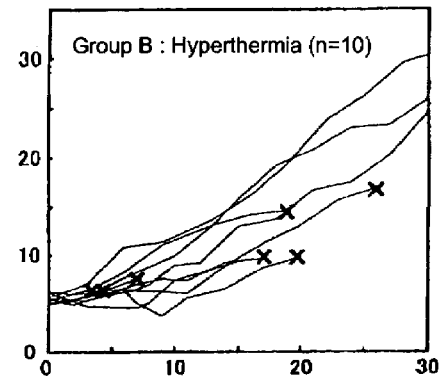
Figure 5:
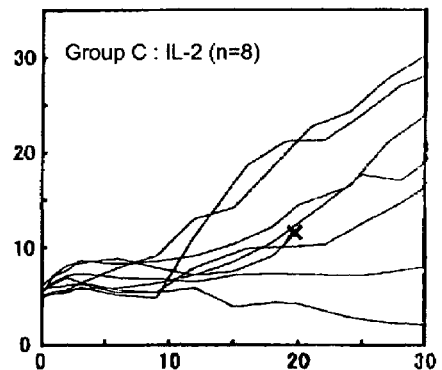
Figure 5:
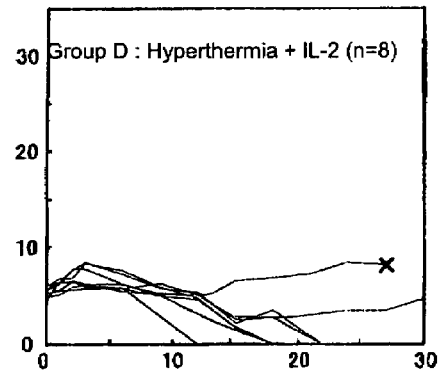

Change in a size of the tumor after injection of MCL is shown in FIG. 5. It shows changes of a size of the tumor in the control group (Group A), hyperthermia group (Group B), IL-2 group (Group C) and the group in which hyperthermia and IL-2 were used in combination (Group D). Day 0 was made a day at which MCL was injected, and a size of the tumor was measured with each 3 days. Incidentally, an average value of a longer size and a shorter size was used for evaluation as a size of the tumor.

In either of the control group, hyperthermia group and IL-2 group, tumor continuously grew. Also, in the case of melanoma, some mice died due to metastasis to lung even when the tumor was not so large.

On the other hand, with regard to the tumor of a group in which hyperthermia and IL-2 were used in combination, the tumor was completely regressed from initiation of therapy till 30 days in 6 mice among 8 mice. Thereafter, the tumor grew again in one mouse. However, with regard to 5 mice in which the tumor was completely regressed, recurrence of the tumor was not observed after 80 days from initiation of the therapy.

Thermotherapy using MCL and administration of IL-2 were carried out in combination against melanoma, it was shown that the tumor tissue alone could be selectively treated, and that complete regression of the tumor tissue could be successively done by carrying out a therapy against the metastasis melanoma effectively.

1-5-3 Survival Term After Therapy

Figure 6:
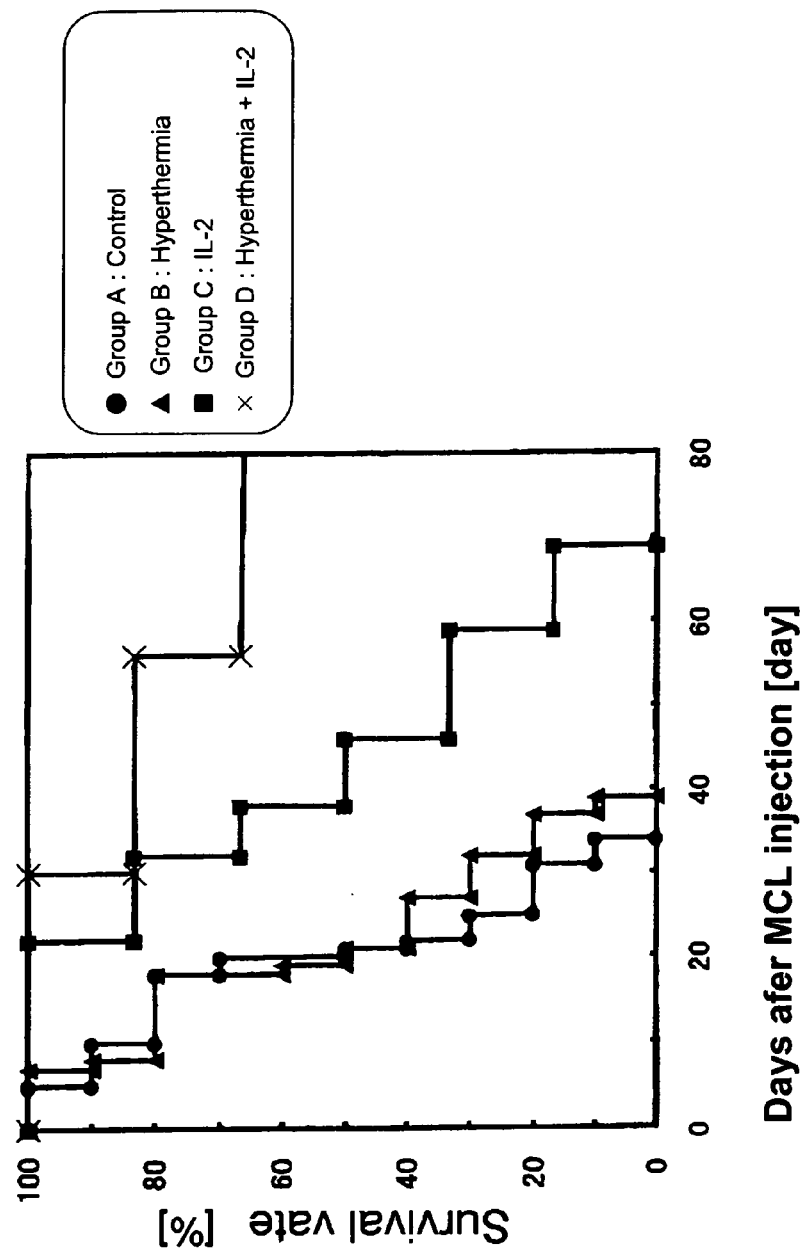
FIG. 6 shows a survival rate of cancer-carried mouse during 80 days after hyperthermia in Example 1. A (control) group (n=10): ●; B (hyperthermia) group (n=10): ▲; C (IL-2) group (n=8): ■; D (hyperthermia+IL-2) group (n=8): X.

A survival rate from initiation of the therapy is shown in FIG. 6. In the control group (Group A), the hyperthermia group (Group B) and the IL-2 group (Group C), all mice died within 80 days from initiation of the therapy due to growth of the tumor or metastasis to lung. However, in the IL-2 group, even when the tumor is large, mice were survived for a long term. This is considered by the reason that by using IL-2, immunological power in a body (activity of immunologically competent cells) is heightened, so that metastasis of melanoma to lung is repressed even when the subcutaneous tumor is grown.

On the other hand, in the group in which hyperthermia and IL-2 were used in combination (Group D), 67% of mice were survived even when 80 days or longer were passed from initiation of the therapy.

From the above facts, it can be considered that systemic anti-tumor immune is induced by carrying out hyperthermia using MCL and administration of IL-2 in combination against the melanoma.

Example 2

Administration of GM-CSF 2-1 Experimental Materials and Experimental Method 2-1-1 Culture of Tumor Cells In the same manner as in 1-1 of Example 1, mouse B16 melanoma cells were used as tumor cells.

2-1-2 Preparation of Magnetite Cationic Liposome (MCL)

In the same manner as in 1-3 of Example 1, magnetite cationic liposome (MCL) was prepared.

2-1-3 Preparation of Cancer-Carried Mouse

B16 melanoma cells cultured by the operation of 2-1-1 and became in a confluent condition were peeled off from the dish by a trypsin treatment, and 4 to 5 ml of a medium was added to stop the reaction. The suspension was collected in centrifuge tubes (available from IWAKI), cells were precipitated by centrifugation (1000 rpm, 5 min) and the medium was removed. Thereafter, cells were suspended in 5 ml of PBS, and washed by removing PBS by centrifugation (1000 rpm, 5 min). This operation was repeated twice, and a pellet of the cells obtained was suspended in PBS.

Next, C57BL/6 (female 4-weeks old) was placed under nembutal anesthesia, and after shaving hair at an upper portion of the right hind leg, 2×10⁶ of B16 melanoma cells were subcutaneously transplanted by using a scalp vein needle (25G×⅝") (available from Terumo Corporation).

2-1-4 Thermatology

Administration of MCL

MCL was injected into a tumor in an amount of 0.1 ml (an iron amount: 2 mg) when a longer size of the tumor reached to about 6 mm. Injection of MCL was directly carried out to the tumor tissue by using a scalp vein needle (25G×⅝") (available from Terumo Corporation). An injection speed was made 0.2 ml/h.

High Frequency Magnetic Field Irradiation

After injection of MCL to the tumor tissue, experimental animals were divided into four groups. Group A is a control group, Group B is a hyperthermia group, Group C is a GM-CSF alone group and Group D is a hyperthermia+GM-CSF group. In Group A and Group C, MCL was injected but no high frequency magnetic field was irradiated. In Group B and Group D, immediately after injection of MCL, a high frequency magnetic field was irradiated. The magnetic field treatment was carried out for 30 minutes, and during the term, a temperature of the tumor surface was maintained to 43° C. by controlling an output of the high frequency magnetic field generating device. At this time, a horizontal type coil was used, and the tumor portion was placed at the center of the coil. A temperature at the surface of the tumor and that of rectum during magnetic field irradiation were measured by using an optical fiber thermometer.

2-1-5 Administration of GM-CSF

Preparation of GM-CSF Solution

As GM-CSF, rhGM-CSF [granulocyte macrophage colony stimulating factor, human, recombinant] (available from Wako Pure Chemical Industries, Ltd.) was used. 10 μg of rhGM-CSF was dissolved in 100 μl of a physiological saline (PBS), to make a concentration of 100 μg/ml.

Administration of GM-CSF

Figure 7:
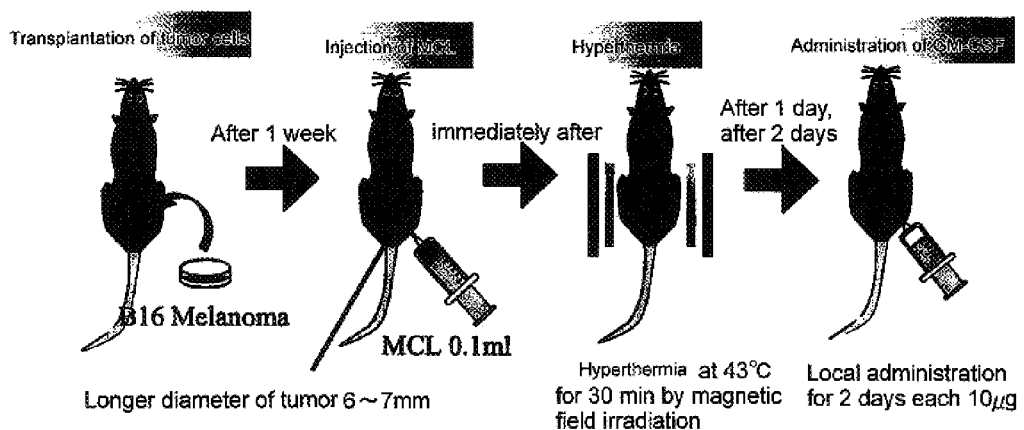
FIG. 7 is a drawing showing a therapeutic scheme from tumor cell transplantation in Example 2.

GM-CSF was injected into the tumor in an amount of each 0.1 ml in the Group C and Group D from the next day of the MCL injection for 2 days continuously. Administration was directly carried out to the tumor tissue by using a scalp vein needle (25G×⅝") (available from Terumo Corporation). An injection speed was made 0.2 ml/h. An injection portion was changed at one day after and two days after, so that the chemical can be administered to the whole part of the tumor tissue as much as possible. A scheme from tumor cells transplantation to therapy is shown in FIG. 7.

2-1-6 Hsp70 Stain at Tumor Tissue

Tissue stain of Hsp70 was carried out with regard to the tumor tissues of the hyperthermia group (Group B) and the control group (Group A). With regard to the hyperthermia group, a mouse one day after the hyperthermia (2 days after injection of MCL), and with regard to the control group, a mouse with the same timing as the hyperthermia group in which 2 days after injection of MCL, were placed under nembutal anesthesia, after removal of blood by circulating physiological saline (PBS) from cardioaorta, the tumor tissue was extirpated. The tumor tissue was washed with PBS and then fixed with formalin (10%).

This specimen was subjected to paraffin embedding in the state of formalin fixation, and then cut out so that the sectional surface became maximum. Thereafter, by using a Hsp70 antibody (available from Santa Cruz Biotechnology Inc., +Santa Cruz, Calif.), the specimen was stained.

Figure 8:
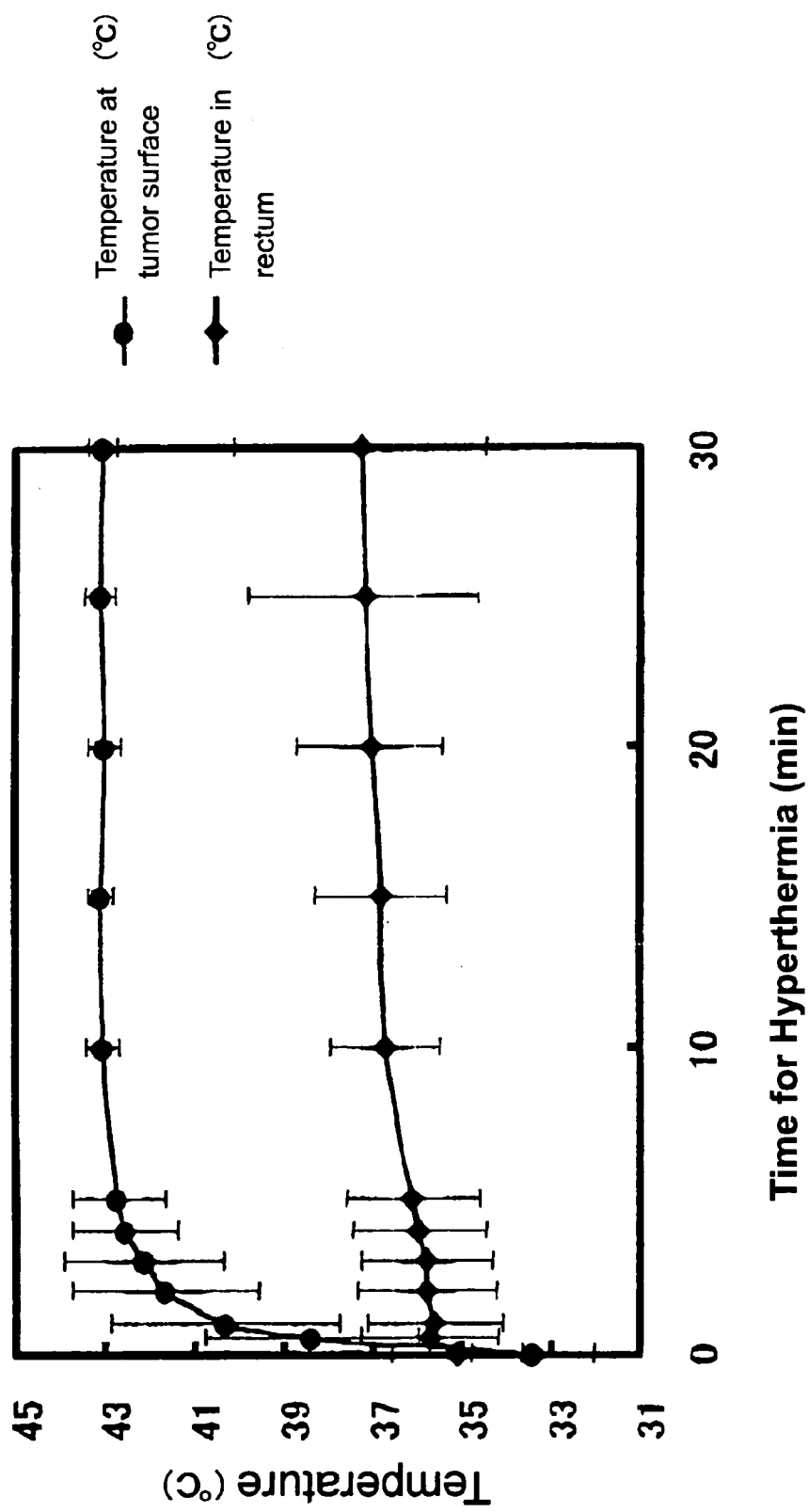
FIG. 8 is a drawing showing temperature change in magnetic field irradiation in Example 2.

2-2 Experimental Results and Consideration 2-2-1 Temperature Change During Magnetic Field Irradiation Temperature change during magnetic field irradiation is shown in FIG. 8. A temperature of the tumor surface was rapidly raised after initiation of irradiation of a high frequency magnetic field, and reached to about 43° C. which has been considered to be effective in hyperthermia. Since the magnetic flux density of the magnetic field generating device in this laboratory can be easily changed by operating an output thereof, so that heat generation of the magnetite was controlled by operating the output. As a result, after the temperature of the tumor surface reached at 43° C., the surface temperature could be maintained at about 43° C., and heated for 30 minutes.

To the contrary, a temperature in rectum was substantially the constant and not raised during irradiation of the magnetic field. That is, in the hyperthermia using MCL, it could be shown that heating could be carried out tumor specifically, and excessive heating could be prevented at the normal tissue.

2-2-2 Change in Size of Tumor with a Lapse of Time

Figure 10A:
FIG. 10A is a schematic drawing showing injecting MCL before therapy.
Figure 10B:
FIG. 10B is a schematic drawing of a hyperthermia+GM-CSF group.
Figure 10C:
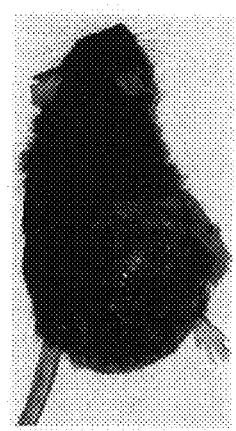
FIG. 10C is a schematic drawing of a control group.

With regard to change in a size of tumor with a lapse of time, the control group is shown in FIG. 9A, the hyperthermia group in FIG. 9B, the GM-CSF alone group in FIG. 10C and the hyperthermia+GM-CSF group in FIG. 9D. The day 0 is a day at which MCL is injected. A size of the tumor (mm) was calculated by (length+width)/2.

The tumor of the control group continued to grow even after injection of MCL. Tumors in the hyperthermia group and the GM-CSF alone group were controlled with a low degree for the first 7 days, but thereafter, they were abruptly started to grow, and the tumor never regressed.

The tumor in the hyperthermia+GM-CSF group was completely regressed in 4 mice among 10 mice after 15 days from injection of MCL, and the remainder that were not completely regressed were controlled in growth of the tumor with a low degree for about 12 days. With regard to those that were completely regressed, the tumor was never recurred thereafter. One example of therapy schedules is shown in FIG. 10A to C. FIG. 10A is a schematic drawing during injecting MCL before therapy. Before therapy, tumor can be observed subcutaneously. FIG. 10B is a schematic drawing of Group D, and shows the state that the tumor was completely regressed after the therapy. No tumor was observed, and remarkable damage was not observed at the peripheral normal portion. FIG. 10C is a schematic drawing of Group A, and shows the state that the tumor was not regressed but increased.

It was shown that, by applying the hyperthermia using MCL and administration of GM-CSF to the melanoma, it was possible to completely regress the primary tumor without causing any damage against the normal portion.

2-2-3 Survival Rate After Initiation of Therapy

Survival rate after initiation of the therapy is shown in FIG. 11. In either of the control group, the hyperthermia group, the GM-CSF alone group, some animals died at about 10 days from initiation of the therapy. These tumors were not so large as less than 15 mm, but when some mice were dissected, metastasis to lung was observed in some mice. It can be considered that a large factor of their death would be metastasis.

On the other hand, in the hyperthermia+GM-CSF group, there is no specimen that died at an early stage, and when the died specimen was dissected, no metastasis was observed. With regard to the specimen died at about 30 to 40 days, a primary tumor was markedly large, these mice lost weight, so that they would die due to weakness.

It could be shown that by using the hyperthermia and a local administration of GM-CSF to the melanoma in combination, there were effects that metastasis that became fatal damage could be repressed.

2-2-4 Tissue Stain of Hsp70 at the Tumor Tissue After Hyperthermia

Tissue stain of Hsp70 at the tumor tissue after hyperthermia is shown in FIGS. 12A and 12B. Hsp70 was stained red with cytoplasm. FIG. 12A is a stained photography of the tumor tissue of the control group (Group A) and FIG. 12B is a stained photography of the tumor tissue of the hyperthermia group (Group B). In the tumor tissue after the hyperthermia, many portions stained red were observed, so that it could be confirmed that Hsp70 had been expressed. On the other hand, in the tumor for control, substantially no red portion was observed. According to the above, it is shown that Hsp70 is expressed in the tumor tissue with a wide range by the hyperthermia, so that it is expected that immune induction will occur due to the effect of Hsp70.

INDUSTRIAL APPLICABILITY

The hyperthermia agent for malignant tumor of the present invention shows higher therapeutic effect against various kinds of malignant tumors as compared with the conventional hyperthermia agents.

The invention claimed is:

1. A method for treating a malignant tumor comprising:
   administering cytokine to said malignant tumor; and
   subjecting said tumor to hyperthermia, wherein
   said subjecting said tumor to hyperthermia comprises administering magnetic fine particles to said tumor and heating said magnetic fine particles;
   said magnetic fine particles comprise magnetite or ferrite or permalloy; and
   the cytokine is interleukin-2.

2. The hyperthermia method according to claim 1, wherein said magnetic fine particles comprise ferrite.

3. The hyperthermia method according to claim 1, wherein said magnetic fine particles comprise permalloy.

4. The hyperthermia method according to claim 1, wherein said magnetic fine particles comprise magnetite.

5. The hyperthermia method according to claim 4, further comprising covering the magnetite with cationic liposome.

6. The hyperthermia method according to claim 4, wherein said magnetic fine particles have an antibody bound on a surface of said magnetic fine particles, said antibody being an antibody which selectively binds to malignant tumor cells.

7. A method for treating a malignant tumor comprising:
   administering cytokine to said malignant tumor; and
   subjecting said tumor to hyperthermia, wherein
   said subjecting said tumor to hyperthermia comprises administering magnetic fine particles to said tumor and heating said magnetic fine particles;
   said magnetic fine particles comprise magnetite or ferrite or permalloy; and the cytokine is a granulocyte macrophage colony stimulating factor.

8. The hyperthermia method according to claim 7, wherein said magnetic fine particles comprise magnetite.

9. The hyperthermia method according to claim 8, further comprising covering the magnetite with cationic liposome.

10. The hyperthermia method according to claim 8, wherein said magnetic fine particles have an antibody bound on a surface of said magnetic fine particles, said antibody being an antibody which selectively binds to malignant tumor cells.

11. The hyperthermia method according to claim 7, wherein said magnetic fine particles comprise ferrite.

12. The hyperthermia method according to claim 7, wherein said magnetic fine particles comprise permalloy.

* * * * *